United States Patent [19]

Flora et al.

[11] Patent Number: 4,491,784
[45] Date of Patent: Jan. 1, 1985

[54] PIEZOELECTRIC MOISTURE MEASURING DEVICE

[75] Inventors: John H. Flora, Lynchburg; James E. Henderson, Concord, both of Va.

[73] Assignee: The Babcock & Wilcox Company, New Orleans, La.

[21] Appl. No.: 413,286

[22] Filed: Aug. 31, 1982

[51] Int. Cl.³ .............................. G01R 27/26
[52] U.S. Cl. ................................ 324/61 QL
[58] Field of Search ........... 324/61 QL, 61 QS, 61 R; 73/29, 73; 331/65

[56] References Cited

U.S. PATENT DOCUMENTS

| | | | |
|---|---|---|---|
| 2,536,111 | 1/1951 | Van Dyke | 324/6 QL |
| 3,256,482 | 6/1966 | Rosso | 324/61 QL |
| 4,344,293 | 8/1982 | Fujiwara et al. | 324/61 QL |

FOREIGN PATENT DOCUMENTS

| | | | |
|---|---|---|---|
| 1340703 | 12/1973 | United Kingdom | 324/61 R |
| 213942 | 10/1968 | U.S.S.R. | 324/61 QL |

Primary Examiner—Stanley T. Krawczewicz
Attorney, Agent, or Firm—Robert J. Edwards; James C. Simmons

[57] ABSTRACT

A moisture-measuring device for measuring moisture of the ambient on one side of a solid wall comprises a piezoelectric crystal sonically coupled to the wall on a surface thereof facing the one side. A capacitor or other moisture sensitive impedance means is connected to the piezoelectric crystal over a network which is operable to provide a response indicative of the impedance of the capacitor upon excitation of the crystal at the resonant frequency of the circuit. The capacitor comprises at least two spaced plates which are exposed to the ambient. Change in moisture in the ambient thus causes change in capacitance of the capacitor. By sonically exciting the piezoelectric crystal from an opposite side of the wall, a measure of change in resonant frequency of the network can be made. This measurement is related to the moisture content of the ambient.

12 Claims, 3 Drawing Figures

PIEZOELECTRIC MOISTURE MEASURING DEVICE

FIELD AND BACKGROUND OF THE INVENTION

The present invention relates, in general, to detection equipment and, in particular, to a new and useful moisture measuring device for measuring moisture of an ambient on one side of a solid wall.

Heavy oil and tar sands represent untapped resources of liquid hydrocarbons which will be produced in increasing quantities to help supplement declining production of conventional crude oil. These deposits must, however, be heated to reduce the oil viscosity before it will flow to the producing wells in economical quantities. The dominant method of heating is by injection of surface generated steam in either a continuous (steam flood) or intermittent (steam stimulation or "huff and puff") mode.

When steam is injected down long injection pipes or "strings", a significant amount of thermal energy is lost to the rock overburden (500 to 7000 feet) which covers the oil deposit. In the initial steam injection projects, the price of oil did not justify the prevention of this heat loss, but now with the price of oil at $30 or more a barrel, insulation systems for the well injection pipe become economically justified.

Several methods are known for determining the state of insulation, and specifically whether insulation used with a component has failed. Such methods include the real time or service monitoring of surface temperature using thermocouples, thermistors, thermometers, optical pyrometers or infrared cameras.

A system of monitoring the input and output fluid temperatures may also be utilized for determining the integrity of the insulation, where the component is designed for conveying a fluid. Additionally, a measurement of power output verses fuel consumption, i.e. efficiency, gives an indication of the state of the insulation since a degraded insulation would reduce efficiency.

In all of the aforementioned techniques, once the component has cooled to ambient temperature, the evidence of thermal failure is no longer present. The techniques must be exercised during real time and thus are limited to cases where real time monitoring is possible and practical.

Off-Line Thermal Testing Techniques are also known which either directly establish the integrity of the insulation or infer this integrity. The component is removed from service for testing.

According to one technique, an induced heat flow using an induction heater is monitored by an infrared camera or other temperature sensing equipment. Alternatively, the component can be placed into a test loop in which thermal efficiency is measured.

Thermal failure can be inferred in an off-line situation by observing the conditions of the component or some part thereof, which has previously been exposed to overheating. Visual inspection may determine severe degradation, for example, warping of the component due to overheating. Discoloration ot the normal surface appearance is also a clue to thermal failure.

Insulated tubing for recovery of oil from tar sands and shale, known as insulated steam injection tubing must have effective insulation to insure adequate efficiency. The tubing is used to inject steam several hundred feet into the earth's crust and reduce viscous hydrocarbons to a fluid state. It is very important to insure the thermal integrity of the tubing and prevent expensive heat loss or the costly removal and replacement of the tube string. A non-destructive method of determining thermal integrity is needed to prevent the use of defective tubes. Since defective tubes invariably acquire moisture, a small moisture detector installed within the insulating chamber would provide a quick and inexpensive quality check for each tube.

Such tubing comprises inner and outer coaxial tubes defining an annular space between the tubes which is provided with insulation means, such as thermal insulation and evacuation of the space to obtain a vacuum. The use of insulation between coaxial tubes is disclosed, for example, in U.S. Pat. No. 3,574,357 to Alexandru et al and U.S. Pat. No. 3,478,783 to Doyle.

SUMMARY OF THE INVENTION

The present invention comprises a capacitive moisture sensor which uses piezo-electric crystals to provide a means of readout without direct electrical contact with the sensor. The invention could be used in any moisture measurement application where ultrasonic transmission is feasible. It is particularly attractive for the inspection of the insulated steam injection tubing since it provides a unique and rugged method of checking tube integrity.

According to the invention, a set of closely spaced electrically conducting plates are connected through a simple electronic network to a piezoelectric crystal. The crystal is bonded and acoustically coupled to an inner wall of an insulated chamber. The piezoelectric crystal can be excited by applying an ultrasonic pressure wave to the outside wall of the chamber. The electrical signal produced at the terminals of the crystal drives the network containing the conducting plates. The capacitance of the conducting plates will effect the electrical characteristics of the network. Since the moisture content of the gas between the conducting plates will have pronounced effect on the capacitance of the plates, an ultrasonic device can be used to measure moisture content from the outside.

One embodiment of the invention includes an induction coil connected in parallel with the capacitive plates. This forms a parallel resonant circuit which tunes the piezoelectric crystal. Moisture content is then determined by measuring the resonant frequency of the crystal. The ultrasonic measurement can be automated by using a sweep frequency modulating pulse generator and automatic peak signal detector. Series resonant inductors and other passive networks can be incorporated with the capacitative plates to enhance the sensitivity of the device.

Another form of the invention incorporates an active network such as an oscillator to sense and transmit moisture measurements. In this case, a relatively low frequency ultrasonic wave could be used to transmit energy to the piezoelectric crystal located inside the insulating chamber. The crystal would transform the ultrasound into an electrical voltage and current. The network receives and rectifies the electrical signal and apply it to an oscillator. The moisture sensitive capacitance plates would control a relatively high frequency oscillation. The oscillator signal would then be applied to the piezoelectric crystal. This would provide an ultrasonic wave that could be easily transmitted through the tube wall to the external transducer. Therefore, a simple measurement of the retransmitted frequency would provide a measure of the moisture content inside the insulating chamber. Various arrangements of piezoelectric crystals and network configurations for receiving and transmission of the ultrasonic signals can be derived.

Accordingly, an object of the present invention is to provide a moisture-measuring device for measuring moisture of an ambient on one side of the solid wall member comprising, a piezoelectric crystal acoustically coupled to the wall member on a surface thereof facing the one side, a capacitor having plate members which are spaced apart, the space being exposed to the ambient and a network connected across the crystal and the plate members and being operable to control the frequency of an oscillator. The oscillator signal is applied to the piezoelectric crystal producing a sonic wave which transmits through the wall to the transducer. The retransmitted frequency is controlled by the moisture content between the capacitor plates which may be said to tune the network.

A further object of the present invention is to provide such a device wherein a passive network using an inductor connected parallel to the capacitor forms a circuit having resonant frequency, which resonant frequency is changed by a change in moisture of the ambient.

A still further object of the invention is to provide a measuring device which is simple in design, rugged in construction and economical to manufacture for measuring moisture on the opposite side of a solid wall member.

DESCRIPTION OF THE PREFERRED EMBODIMENTS

Figure 1:
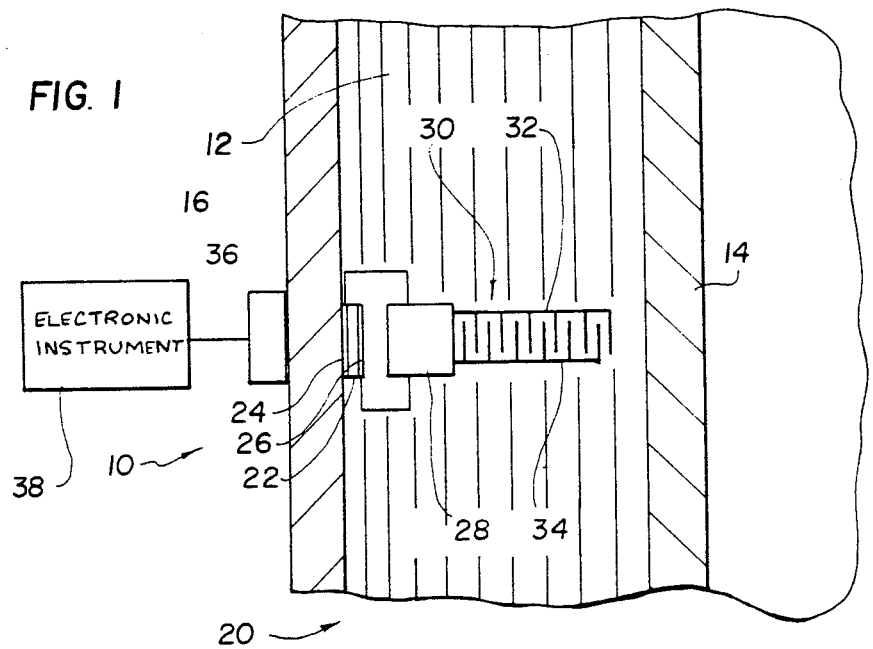
FIG. 1 is a schematic representation of the invention disposed in the space between inner and outer walls of tubing.

Referring to the drawings, in particular, the invention embodied therein, in FIG. 1, comprises a moisture measuring or detecting device generally designated 10 which detects the presence of moisture in an insulation layer 12 between an inner wall or tube 14 and an outer wall or tube 16. Tubes 14,16 with insulation 12 may be of the insulated steam injection tube type for injecting steam into an oil well, and is generally designated 20.

The device proper comprises a piezoelectric crystal 22. Crystal 22 may, for example, be quartz. As shown, crystal 22 includes electrodes or plates 24, and 26. The piezoelectric axis is selected to extend between these electrodes so that the crystal has electrode faces which are so-called X-cut. Electrodes 24,26 of crystal 22 are connected to a network 28 to be described hereinunder.

Network 28 is, in turn, connected to a capacitor 30 having a pair of spaced plate members 32 and 34. The space between plate members 32, 34 is exposed to the ambient in insulation layer 12 on one side of outer wall 16.

Plate members 32 and 34 are each formed of a plurality of parallel and interspaced plates.

According to the invention, piezoelectric crystal 22 is excited by an ultrasonic transducer 36 which is connected to an electronic instrument 38. Ultrasonic instrument 38 and transducer 36 are of known type and discussed for example in the publication STEAM, ITS GENERATION AND USE, 39th edition, 1978, the Babcock & Wilcox Company.

By applying a signal having an ultrasonic frequency to transducer 36, the sonic waves pass through wall 16 and vibrate piezoelectric crystal 22. To improve this effect, piezoelectric crystal 22 is bonded to and sonically coupled with the inner surface of wall 16. The ultrasonic wave is then transferred into an electrical signal having the same frequency which is processed through network 28 and applied to capacitor 30. Since moisture content of the ambient within the insulation layer 12 affects the capacitance C of capacitor 30, the impedance of the network inside the annulus is affected. This change in impedance can be detected by electronic instrument 38 using transducer 36 by a signal being provided upon exitation thereof at its resonant frequency. With a moisture-free desired ambience within insulation layer 12, one response is obtained, whereas, with moisture in layer 12, which indicates a failure or degradation of insulation, a different response is obtained.

Figure 2:
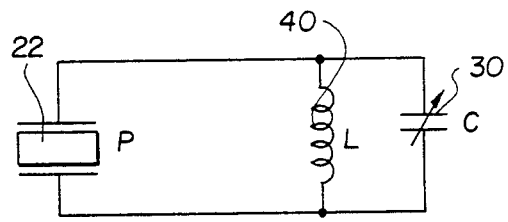
FIG. 2 is a schematic representation of a circuit according to one embodiment of the invention.

Referring to FIG. 2, one example of network 28 is a parallel connected inductor 40 having an inductance L. Capacitor 30 is shown to be variable, which variation is caused by any change in the ambient of the insulation layer, in particular its moisture content. The network of FIG. 2 functions as an oscillator having a natural or resonant frequency $\omega_o$. This frequency is established according to the following relationship:

$$\omega_o = \frac{1}{\sqrt{LC}}.$$

For a known moisture-free ambient between inner and outer walls 14, 16, the natural or resonant frequency is known. With electronic instrument 38 and transducer 36, exciting peizoelectric crystal 22 at that natural frequency, a peak in the network response will be generated. If the natural frequency of the circuit in FIG. 2 drifts from the moisture-free value, in particular if the capacitance decreases due to an increase in moisture, an increased natural frequency will be produced which will require a shifting of the frequency applied to piezoelectric 22, before resonance is determined. Electronic instrument 38, for this purpose, can be provided with a sweep frequency modulating pulse generator and an automatic peak signal detector. An example of such equipment is known as the Tektronix model FG504.

Figure 3:
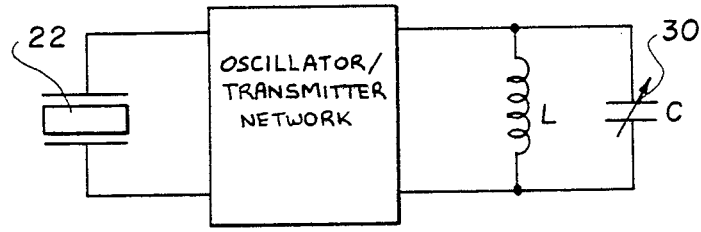
FIG. 3 is a schematic representation of a circuit according to another embodiment of the invention.

Referring now to FIG. 3, the change in capacitance tunes the piezoelectric cyrstal to thus provide a response which can be sensed for measurement of moisture content. A voltage generated at the crystal activates the network. A detector detects when the voltage is built up to a certain level and switches back for the oscillator to send a signal back out and its frequency read.

Instead of a capacitor, any other moisture sensitive impedance means can be used which changes impedance with change in moisture. Other devices can for example be a moisture sensitive resistor or a lithium chloride humidity cell. Impedance is meant to include non-linear as well as linear electrical characteristics.

It is also noted that the terms "ultrasonic" and "sonic" are used interchangeably herein and are meant to mean not only sound or pressure waves which are within the range of hearing but pressure waves which are above and below the range of hearing and generally any pressure waves which can be transmitted through a medium.

The annular space between the inner and outer tubes or tubulars may advantageously be filled with fibrous or layered insulation, and/or evacuated to establish a thermal barrier. The space, when evacuated, may also be provided with a getter material which absorbs gases that may migrate into the space, to maintain the vacuum. Such gases include hydrogen from corrosion of the outer tube and $N_2$, Co or $O_2$ which is outgassed from the inner tube. The getter material (e.g. titanium) is placed adjacent the inner tube so as to be exposed to the elevated steam temperature of 400° to 700° F., and thus activated to more effectively absorb the gases.

While specific embodiments of the invention have been shown and described in detail to illustrate the application of the principles of the invention, it will be understood that the invention may be embodied otherwise without departing from such principles.

What is claimed is:

1. A moisture-measuring device for measuring moisture of an ambient on one side of a solid wall member comprising:
    a piezoelectric crystal sonically coupled to the wall member on a surface thereof facing the one side;
    a capacitor having two plate members which are spaced apart, the space between the two plate members being exposed to the ambient; and
    a network connected across said capacitor and crystal to provide a response indicative of the impedance of the capacitor upon excitation of the crystal at the resonant frequency of the network;
    whereby exposure of the capacitor to a moisture variation results in a change in the response obtained upon excitation of the crystal from an opposite side of the wall.

2. A device according to claim 1, wherein each of said plate members of said capacitor comprises a plurality of parallel plates, parallel plates of said two plate members being interspaced with each other.

3. A device according to claim 2, including a sonic transducer engaged on a surface of the solid wall on the opposite side thereof and means for sonically activating said transducer to sonically excite said crystal.

4. A device according to claim 1, including a sonic transducer engaged on a surface of the solid wall on the opposite side thereof and means for sonically activating said transducer to sonically excite said crystal.

5. A device according to claim 4, including a frequency modulating pulse generator and an automatic peak signal detector included in said means for activating said transducer for sweeping a frequency range.

6. A device according to claim 5, wherein said network comprises an inductor connected in parallel to said capacitor, said capacitor and inductor forming a circuit having resonant frequency, said resonant frequency changing with a change of moisture in the ambient to change a peak frequency sensed by said automatic peak signal detector.

7. A device according to claim 1, wherein said piezoelectric crystal is X-cut, said crystal having a pair of electrodes, one of which is bonded to the surface of the wall member facing the one side.

8. A device according to claim 1, wherein said wall member comprises an outer tubular having an inner surface to which said piezoelectric crystal is sonically coupled, an inner tubular spaced inwardly of said outer tubular and surrounded by said outer tubular and defining an annular space therewith and insulation in said annular space, said inner tubular adapted for conveying steam to an oil well, said capacitor having said two plate members disposed in said insulation and exposed to the ambient in said insulation.

9. A method of measuring moisture in an ambient on one side of a wall with a piezoelectric crystal sonically coupled to the wall on a surface thereof facing the ambient, a network connected to the crystal, and a capacitor connected to the network, the capacitor having a pair of spaced plate members exposed to the ambient, the method comprising:
    sonically exciting the crystal from an opposite side of the wall at various frequencies until a response is obtained upon excitation thereof at the resonant frequency of the network which response is indicative of the impedance of the capacitor which is in turn indicative of a change in the ambient.

10. A method according to claim 9, wherein the wall with the piezoelectric crystal sonically coupled thereto comprises an outer tubular, the piezoelectric crystal sonically coupled to an inner surface of the outer tubular, an inner tubular spaced inwardly and surrounded by said outer tubular and connected therewith to define an annular space, insulation in said annular space in which said pair of spaced capacitor plate members are disposed, said inner tubular adapted to convey steam to an oil well.

11. A moisture-measuring device for measuring moisture of an ambient on one side of a solid wall member comprising:
    a piezoelectric crystal sonically coupled to the wall member on a surface thereof facing the one side;
    moisture sensitive impedance means exposed to the ambient; and
    a network connected across said moisture sensitive impedance means and to said piezoelectric crystal to provide a response indicative of the impedance of said moisture sensitive impedance means upon excitation of the crystal;
    whereby exposure of said moisture sensitive impedance means to a moisture variation results in a change in the response obtained upon excitation of said crystal from an opposite side of the wall.

12. A device according to claim 11 including a signal generating and transmitting means, and wherein the crystal, upon excitation thereof, transforms sonic waves into electrical energy and applies the energy to said generating and transmitting means which in turn transmits a signal indicative of the impedance of the moisture sensitive impedance means.

* * * * *